US012165240B2

(12) United States Patent
Katsevich et al.

(10) Patent No.: US 12,165,240 B2
(45) Date of Patent: Dec. 10, 2024

(54) SYSTEM AND METHOD USING TOMOGRAPHIC MULTI-MODALITY THREE-DIMENSIONAL IMAGING TO ESTIMATE MEDIUM PARAMETERS

(71) Applicants: University of Central Florida Research Foundation, Inc., Orlando, FL (US); iTomography Corporation, Barker, TX (US)

(72) Inventors: Alexander Katsevich, Oviedo, FL (US); Michael Frenkel, Barker, TX (US); Igor Frenkel, Houston, TX (US); Airidas Korolkovas, Houston, TX (US); Seongjin Yoon, Houston, TX (US)

(73) Assignees: University of Central Florida Research Foundation, Inc., Orlando, FL (US); iTomography Corporation, Barker, TX (US)

( * ) Notice: Subject to any disclaimer, the term of this patent is extended or adjusted under 35 U.S.C. 154(b) by 575 days.

(21) Appl. No.: 17/448,150

(22) Filed: Sep. 20, 2021

(65) Prior Publication Data

US 2022/0092831 A1  Mar. 24, 2022

Related U.S. Application Data

(60) Provisional application No. 63/080,622, filed on Sep. 18, 2020.

(51) Int. Cl.
*G01N 23/046* (2018.01)
*G01N 33/24* (2006.01)
*G06N 20/00* (2019.01)
*G06T 11/00* (2006.01)
*G16H 30/40* (2018.01)
*A61B 6/03* (2006.01)

(52) U.S. Cl.
CPC .......... *G06T 11/003* (2013.01); *G01N 23/046* (2013.01); *G01N 33/241* (2013.01); *G06N 20/00* (2019.01); *G16H 30/40* (2018.01); *A61B 6/032* (2013.01)

(58) Field of Classification Search
CPC .. G06T 11/003; G01N 23/046; G01N 33/241; G06N 20/00; G16H 30/40; A61B 6/032
See application file for complete search history.

(56) References Cited

U.S. PATENT DOCUMENTS 10,997,327 B2    5/2021   Fredrich et al.
11,151,759 B2 *  10/2021  Vija ....................... G01T 1/161
(Continued)

OTHER PUBLICATIONS

P. Cosenza, D. Prêt, and M. Zamora (2015): "Effect of the local clay distribution on the effective electrical conductivity of clay", Journal of Geophysical Research: Solid Earth.
(Continued)

*Primary Examiner* — Manuel A Rivera Vargas
(74) *Attorney, Agent, or Firm* — Molly L. Sauter; Smith & Hopen, P.A.

(57) ABSTRACT

In various embodiments, the present invention provides a multi-modality imaging system in combination with a novel imaging method comprising complex modeling of the modalities and machine learning. In a particular embodiment, multi-modality imaging of a large rock core is described.

29 Claims, 6 Drawing Sheets

(56) References Cited

U.S. PATENT DOCUMENTS

2018/0018757 A1* 1/2018 Suzuki .................. G06N 3/045
2019/0295294 A1* 9/2019 Fournie ................ G06T 11/006
2020/0279411 A1* 9/2020 Atria .................... G06T 11/006
2020/0320753 A1* 10/2020 Feng ..................... A61B 6/037

OTHER PUBLICATIONS

Eduardo I. Jussiani, Carlos R. Appoloni (2014): "Effective atomic number and density determination of rocks by X-ray microtomography", Micron 70 (2015) 1-6.
Michael Zhdanov (2008): "Generalized effective-medium theory of induced polarization", Geophysics, 73(5).
Juergen H. Schön (2011): "Physical Properties of Rocks", Elsevier, 702p (Classical Book on Rock Properties and Applications in the Petroleum Industry).

* cited by examiner

100

```
┌─────────────────────────────────────────────────────────────────────┐
│   PROVIDING A PLURALITY OF MODELS OF AN OBJECT OF INTEREST, EACH OF │
│   THE PLURALITY OF MODELS COMPRISING ONE OR MORE PREDETERMINED      │
│                       MATERIAL PROPERTIES                           │
│                               105                                   │
└─────────────────────────────────────────────────────────────────────┘
                                  ↓
┌─────────────────────────────────────────────────────────────────────┐
│   COMPUTING AN X-RAY COMPUTED TOMOGRAPHY (CT) RECONSTRUCTION FOR    │
│   EACH OF THE PLURALITY OF MODELS ON A 3D GRID BY COMPUTING ONE OR  │
│   MORE EFFECTIVE MATERIAL PROPERTIES OF THE MODELS THAT A SELECTED  │
│   X-RAY CT SCANNING INSTRUMENT IS SENSITIVE TO FOR EACH OF THE      │
│   PLURALITY OF MODELS WITH A 3D GRID STEP SIZE CORRESPONDING TO THE │
│        SELECTED X-RAY CT SCANNING INSTRUMENT RESOLUTION             │
│                               110                                   │
└─────────────────────────────────────────────────────────────────────┘
                                  ↓
┌─────────────────────────────────────────────────────────────────────┐
│   COMPUTING AN ELECTROMAGNETIC (EM) RECONSTRUCTION FOR EACH OF THE  │
│   PLURALITY OF MODELS ON A 3D GRID BY COMPUTING ONE OR MORE         │
│   EFFECTIVE MATERIAL PROPERTIES OF THE MODELS THAT A SELECTED EM    │
│   TOMOGRAPHY SCANNING INSTRUMENT IS SENSITIVE TO FOR EACH OF THE    │
│   PLURALITY OF MODELS WITH A 3D GRID STEP SIZE CORRESPONDING TO THE │
│         SELECTED EM TOMOGRAPHY SCANNING INSTRUMENT RESOLUTION       │
│                               115                                   │
└─────────────────────────────────────────────────────────────────────┘
                                  ↓
┌─────────────────────────────────────────────────────────────────────┐
│   TRAINING A MACHINE LEARNING PREDICTION MODEL TO ESTIMATE A VALUE  │
│   OF ONE OR MORE OF THE MATERIAL PROPERTIES FOR EACH OF THE         │
│   PLURALITY OF MODELS ON A 3D GRID HAVING A DESIRED 3D GRID STEP    │
│   SIZE, WHEREIN THE ESTIMATE OF THE VALUE OF THE ONE OR MORE        │
│   MATERIAL PROPERTIES IS DETERMINED BASED UPON THE COMPUTED X-RAY   │
│   CT RECONSTRUCTION AND COMPUTED EM RECONSTRUCTION OF EACH OF THE   │
│   PLURALITY OF MODELS (OPT. THE MACHINE LEARNING PREDICTION MODEL   │
│   COMPRISES AN EMPIRICAL FUNCTION TO CONVERT THE ONE OR MORE        │
│   EFFECTIVE MATERIAL PROPERTIES OF THE ONE OR MORE OBJECTS OF       │
│   INTEREST THAT THE SELECTED X-RAY CT SCANNING INSTRUMENT IS        │
│   SENSITIVE TO AND THE ONE OR MORE EFFECTIVE MATERIAL PROPERTIES    │
│   OF THE ONE OR MORE OBJECTS OF INTEREST THAT THE SELECTED EM       │
│   TOMOGRAPHY SCANNING INSTRUMENT IS SENSITIVE TO INTO THE ESTIMATE  │
│   OF THE VALUE OF THE ONE OR MORE MATERIAL PROPERTIES THAT BOTH     │
│   THE SELECTED X-RAY CT SCANNING INSTRUMENT AND THE SELECTED EM     │
│         TOMOGRAPHY SCANNING INSTRUMENT ARE NOT SENSITIVE TO)        │
│                               120                                   │
└─────────────────────────────────────────────────────────────────────┘
```

PROVIDING A SECOND PLURALITY OF MODELS OF THE OBJECT OF INTEREST
205

REPEATING COMPUTING THE X-RAY CT RECONSTRUCTION FOR EACH OF THE SECOND PLURALITY OF MODELS OF THE OBJECT OF INTEREST AND REPEATING COMPUTING THE EM RECONSTRUCTION FOR EACH OF THE SECOND PLURALITY OF MODELS OF THE OBJECT OF INTEREST TO TEST AN ACCURACY OF THE MACHINE LEARNING PREDICTION MODEL BY COMPARING THE ESTIMATED VALUES OF THE ONE OR MORE MATERIAL PROPERTIES WITH THE ONE OR MORE MATERIAL PROPERTIES COMPUTED FROM THE PLURALITY OF MODELS
210

MODIFYING THE 3D GRID STEP SIZE CORRESPONDING TO THE SELECTED X-RAY INSTRUMENT RESOLUTION, THE 3D GRID STEP SIZE CORRESPONDING TO A SELECTED ELECTROMAGNETIC (EM) TOMOGRAPHY SCANNING INSTRUMENT RESOLUTION AND THE DESIRED 3D GRID STEP SIZE TO OPTIMIZE THE MACHINE LEARNING PREDICTION MODEL
215

FIG. 2

SYSTEM AND METHOD USING TOMOGRAPHIC MULTI-MODALITY THREE-DIMENSIONAL IMAGING TO ESTIMATE MEDIUM PARAMETERS

CROSS-REFERENCE TO RELATED APPLICATIONS

This application claims priority to currently pending U.S. Provisional Patent Application No. 63/080,622 filed on Sep. 18, 2020 and entitled "System And Method Using Multi-Modality Imaging To Estimate Effective Medium Parameters", the entirety of which is incorporated herein by reference.

BACKGROUND OF THE INVENTION

X-ray Computed Tomography (CT) is a common and versatile imaging modality used to differentiate materials based on their density, for example, water and a solid material such as quartz. However, the ability to differentiate various materials using CT imaging, including Multi-Energy Computed Tomography (MECT) imaging, is limited.

In particular, rock cores, which are used for formation evaluation in the petroleum industry, are generally composed of a dense, solid matrix, interwoven with a network of small pores that are in turn filled with a mixture of water and hydrocarbons (HC). It is challenging to develop a system for accurately estimating, in a volumetric fashion, the distribution of HC in large rock cores (e.g., 3-4-inch diameter and 3-4-ft long) that is sufficiently fast for making operational decisions at the wellsite. For example, X-ray attenuation of oil and water differs by only ~10%, which is very faint compared to the difference between water and a solid material like quartz, which is ~300%. In addition, rock pores can be smaller than the resolution of the CT or micro-CT scanners. All in all, it is not feasible to accurately (e.g., with higher than 90% accuracy) estimate HC distribution throughout a large core with a high core scanning and analysis throughput (e.g., faster than 1 meter/hour) by performing wellsite Digital Rock (DR) analysis of volumes generated by a single imaging modality such as micro-CT.

Fast volumetric estimation of the distribution of HC in large rock cores is only one example illustrating a potential difficulty in differentiating materials using CT and micro-CT imaging as a single imaging modality. Examples exist in other fields, including, but not limited to, medical imaging, pre-clinical imaging, dental imaging, luggage scanning, and various other Non-Destructive Testing (NDT) applications of X-ray CT-based technologies.

Accordingly, what is needed in the art is an improved system and method that provides accurate and fast volumetric imaging of objects comprising two or more materials that are difficult to differentiate. In particular, a system and method allowing for fast scanning of a rock core of a large diameter and length immediately after extraction from a well, and then performing accurate and fast volumetric assessment of its HC content for making wellsite operational decisions is strongly needed by the petroleum industry.

SUMMARY OF THE INVENTION

In various embodiments, the present invention provides a system and method that combines imaging modalities based on different physics, e.g., X-ray CT, X-Ray Diffraction (XRD), and an Electromagnetic (EM)-based Tomography (EMT), such as Electrical Impedance Tomography (EIT), Magnetic Induction Tomography (MIT), or Electrical Capacitance Tomography (ECT), or others. The invention additionally supports the multi-modality systems by providing a method describing a novel imaging workflow, complex modeling of the utilized modalities, and machine learning (ML).

In one embodiment, the present invention provides a computer implemented method for training a machine learning prediction model for performing multi-modality non-destructive tomographic imaging of an object of interest. The method includes, providing a plurality of models of an object of interest, each of the plurality of models comprising one or more predetermined material properties. The method further includes, computing an X-ray Computed Tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray instrument resolution and computing an Electromagnetic (EM) reconstruction for each of the plurality of models on a 3D grid by computing one or more effective material properties of the models that a selected EM Tomography scanning instrument is sensitive to for each of the plurality of models with a 3D grid step size corresponding to the selected EM Tomography scanning instrument resolution. The method continues by training a machine learning prediction model to estimate a value of one or more of the material properties for each of the plurality of models on a grid having a desired 3D grid step size, wherein the estimate of the value of the one or more material properties is determined based upon the computed X-ray CT reconstruction and computed EM reconstruction of each of the plurality of models.

In a particular embodiment, the machine learning prediction model of the present invention includes an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

Following the training of the machine learning prediction model for performing multi-modality non-destructive tomographic imaging of an object of interest, the method continues in an operational phase by performing an X-ray CT scan of the object of interest to generate X-ray CT scan data of one or more objects of interest and performing an EM Tomography scan of the object of interest to generate EM Tomography scan data of the one or more objects of interest. The method continues by, reconstructing the one or more effective material properties of the models that the selected X-ray CT scanning instrument is sensitive to for the one or more objects of interest by inverting the X-ray scan data on the 3D grid having the 3D grid step size corresponding to the selected X-ray CT instrument resolution, reconstructing the one or more effective material property of the models that the selected EM Tomography scanning is sensitive to for the one or more objects of interest by inverting the EM Tomography scan data on the 3D grid having the 3D grid step size corresponding to the selected EM Tomography scanning instrument resolution and using the machine learning prediction model to estimate the value of the one or more material properties for the one or more objects of interest on the 3D grid having the desired 3D grid step size.

In a specific embodiment, the one or more objects of interest may be a rock core and the estimate of the value of the one or more material properties may be a value of a hydrocarbon (i.e., oil and/or gas), or other fluids content in the rock core, which is important information for reserve estimation in hydrocarbon exploration and hydrocarbon production. In the present invention, the term rock core (or, core) means any solid mass of geological materials extracted from the ground, e.g., from the well, from underground, or from an outcrop on the surface of the Earth (or another planet). In particular, this may include rock cuttings, etc.

In a specific embodiment, the estimate of the value of the one or more material properties of the rock core is performed at a wellsite within a timeframe such that the rock core is in substantially the same condition as it was in the ground, wherein substantially the same condition means that the hydrocarbon (HC) saturation inside the core has not significantly changed.

In an additional embodiment, the present invention provides a computer implemented method for performing multi-modality non-destructive tomographic imaging of one or more objects of interest. The method includes, performing an X-ray Computer Tomography (CT) scan of one or more objects of interest using a selected X-ray CT instrument to generate X-ray CT scan data of the one or more objects of interest and performing an EM Tomography scan of the one or more objects of interest using a selected EM Tomography scanning instrument to generate EM Tomography scan data of the one or more objects of interest. The method further includes, reconstructing one or more effective material properties of the one or more objects of interest that the selected X-ray CT scanning instrument is sensitive to by inverting the X-ray CT scan data on a 3D grid having a 3D grid step size corresponding to a resolution of the selected X-ray CT instrument, reconstructing one or more effective material properties of the one or more objects of interest that the selected EM Tomography scanning instrument is sensitive to by inverting the EM Tomography scan data on a 3D grid having a 3D grid step size corresponding to a resolution of the selected EM Tomography scanning instrument resolution and using a machine learning prediction model to estimate a value of one or more material properties for the one or more objects of interest on a 3D grid having a desired 3D grid step size. In this embodiment, the machine learning prediction model includes an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

In a specific embodiment, the one or more objects of interest may be a rock core and the estimate of the value of the one or more material properties may be a value of a hydrocarbon content of the rock core.

In an additional embodiment, the present invention provides one or more non-transitory computer-readable media having computer-executable instructions for performing computer-executable instructions for performing a method of running a software program on a computing device for training a machine learning prediction model for providing a multi-modality non-destructive tomographic imaging method for one or more objects of interest. The method for training the machine learning prediction model issues instructions from the software program for providing a plurality of models of an object of interest, each of the plurality of models comprising one or more predetermined material properties. The instructions further include, computing an X-ray Computed Tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray instrument resolution, computing an Electromagnetic (EM) reconstruction for each of the plurality of models on a 3D grid by computing one or more effective material properties of the models that a selected EM Tomography scanning instrument is sensitive to for each of the plurality of models with a 3D grid step size corresponding to the selected EM Tomography scanning instrument resolution and training a machine learning prediction model to estimate a value of one or more of the material properties for each of the plurality of models on a grid having a desired 3D grid step size, wherein the estimate of the value of the one or more material properties is determined based upon the computed X-ray CT reconstruction and computed EM reconstruction of each of the plurality of models.

In a particular embodiment, the software implementing the machine learning prediction model includes an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

Following the training of the machine learning prediction model, in an operational mode, the media further includes issuing instructions from the software program for performing an X-ray CT scan of the object of interest to generate X-ray CT scan data of one or more objects of interest, performing an EM Tomography scan of the object of interest to generate EM Tomography scan data of the one or more objects of interest, reconstructing the one or more effective material properties of the models that the selected X-ray CT scanning instrument is sensitive to for the one or more objects of interest by inverting the X-ray scan data on the 3D grid having the 3D grid step size corresponding to the selected X-ray CT instrument resolution, reconstructing the one or more effective material property of the models that the selected EM Tomography scanning is sensitive to for the one or more objects of interest by inverting the EM Tomography scan data on the 3D grid having the 3D grid step size corresponding to the selected EM Tomography scanning instrument resolution and using the machine learning prediction model to estimate the value of the one or more material properties for the one or more objects of interest on the 3D grid having the desired 3D grid step size.

In a specific embodiment, the one or more objects of interest may be a rock core and the estimate of the value of the one or more material properties may be a value of a hydrocarbon content of the rock core.

Accordingly, in various embodiments, the present invention provides an improved system and method for accurate and fast volumetric imaging of objects comprising two or more materials that are difficult to differentiate. In particular, a system and method allowing for fast scanning of a rock core of a large diameter and length immediately after extraction from a well, and then performing accurate and fast volumetric assessment of its HC content for making wellsite operational decisions is provided.

BRIEF DESCRIPTION OF THE FIGURES

FIG. 1 is a flow diagram illustrating a training stage of the multi-modality imaging system, in accordance with an embodiment of the present invention.

FIG. 2 is a flow diagram illustrating additional steps in the training stage of the multi-modality imaging system shown in FIG. 1, in accordance with an embodiment of the present invention.

DETAILED DESCRIPTION OF THE INVENTION

Figure 3:
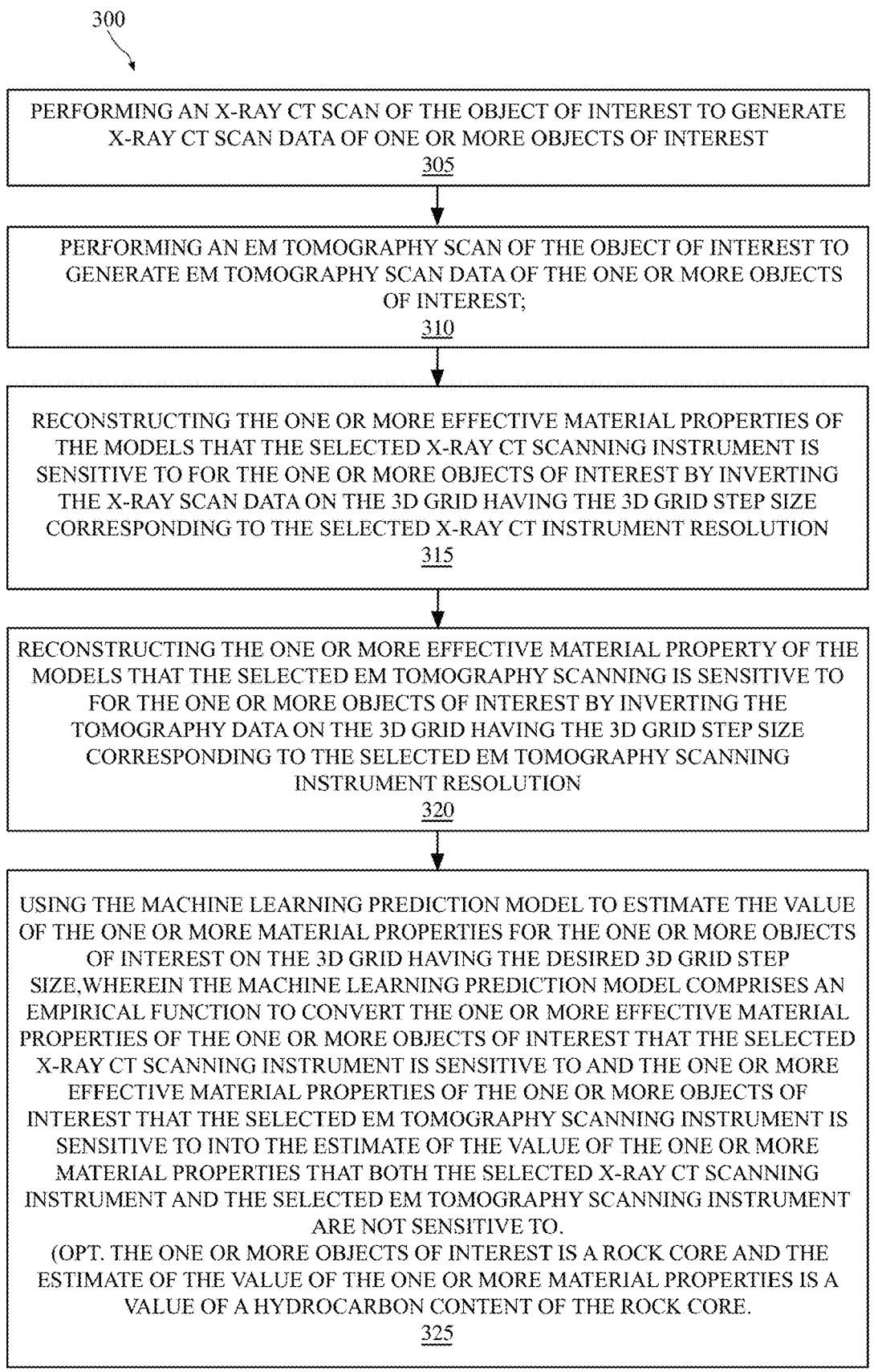
FIG. 3 is a flow diagram illustrating an operational stage of the multi-modality imaging system, in accordance with an embodiment of the present invention.

One objective of the present invention is to overcome known challenges in the imaging of an object comprising components that are not easily differentiated by CT scanning. Additionally, the present invention provides a solution that can be performed onsite to facilitate efficient imaging and assessment of an object of interest. Additionally, the present invention provides a method that allows for the accurate estimation of effective parameters of the medium in an indirect way from low resolution scan data. Estimation of such parameters directly with a conventional approach would require a scan with a much higher resolution.

In one embodiment, the present invention generates accurate images of effective water and oil saturation distributions inside large rock core samples, at a speed required for wellsite operations. The embodiment combines complementary advantages of two or more different physical tomographic imaging modalities, powered by a novel core imaging workflow, includes complex modeling of the utilized modalities, and utilizes machine learning.

The present invention may be described as comprising a training stage and an operational stage. The training stage may be executed using a combination of models of an object of interest and laboratory measurements. The operational stage provides for the practical implementation of the system, such as at a wellsite for imaging of large rock cores.

FIG. 1 illustrates a flow diagram 100 describing the training stage of the present invention which provides a method for training a machine learning prediction model for performing multi-modality non-destructive tomographic imaging of an object of interest.

At operation 105 of FIG. 1, the method begins by providing a plurality of models of an object of interest, each of the plurality of models comprising one or more predetermined material properties.

The method continues at operation 110 by computing an X-ray computed tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray CT scanning instrument resolution. The selected X-ray CT scanning instrument may be a multi-energy computed tomography (MECT) instrument. The one or more effective material properties of the models that the selected X-ray CT scanning instrument is sensitive may include electron density and effective atomic number.

In the present invention, the term MECT includes Dual-Energy CT (DECT), Triple-Energy CT (TECT), etc., and generally refers to probing the object of interest in a tomographic manner by X-ray beams with two or more different spectra.

In the present invention, the term "computing a reconstruction" in the context of X-ray CT scanning, EM Tomography scanning, and other types of scanning is understood in the general sense, i.e. it includes applying the appropriate reconstruction algorithm to compute the property of the medium that the modality is sensitive to and by computing this property directly from the ground truth model of the object. An example of the latter is computing the average electron density in a voxel of a size commensurate with the instrument resolution from the knowledge of the true electron density at every point of the voxel that is available as part of the model of the object (also known as the ground truth model). Such computation can be realistic (i.e., it may include simulating various inaccuracies inherent in reconstruction from real data) or idealized (i.e., it may ignore various inaccuracies inherent in reconstruction from real data).

The method continues at operation 115 by computing an electromagnetic (EM) reconstruction for each of the plurality of models on a 3D grid by computing one or more effective material properties of the models that a selected EM Tomography scanning instrument is sensitive to for each of the plurality of models with a 3D grid step size corresponding to the selected EM tomography scanning instrument resolution. In the present invention, the term "Electromagnetic" and the abbreviation "EM" refer to any modality within the range of electrical, electromagnetic, and other similar, i.e., any electricity and/or magnetism related tomographic modality. The selected EM Tomography scanning instrument may be an electrical impedance tomography (EIT) instrument. The one or more effective material properties of the models that the selected EM Tomography scanning instrument is sensitive to may be selected from an effective scalar conductivity and an effective tensor conductivity.

The method concludes at operation 120 by training a machine learning prediction model to estimate a value of one or more of the material properties for each of the plurality of models on a 3D grid having a desired 3D grid step size, wherein the estimate of the value of the one or more material properties is determined based upon the computed X-ray CT reconstruction and computed EM reconstruction of each of the plurality of models. Optionally, the machine learning prediction model comprises an empirical function to convert the one or more effective material properties of the one or more objects of interest that the selected X-ray CT scanning instrument is sensitive to and the one or more effective material properties of the one or more objects of interest that the selected EM tomography scanning instrument is sensitive to into the estimate of the value of the one or more material properties that both the selected X-ray CT scanning instrument and the selected EM tomography scanning instrument, if each is applied in a single modality imaging mode, are not sensitive to.

In a specific embodiment, training the machine learning prediction model to determine the estimate of the value of the one or more material properties for each of the plurality of models on the 3D grid having a desired 3D grid step size may further include, obtaining an empirical function to convert the one or more effective material properties of the models that the selected X-ray CT scanning instrument is sensitive to and the one or more effective material properties of the models that the selected EM tomography scanning instrument is sensitive to into the estimate of the value of the one or more material properties. Alternatively, training the machine learning prediction model to determine the estimate of the value of the one or more material properties for each of the plurality of models on the 3D grid having a desired 3D grid step size may further include, training a neural network to convert the one or more effective material properties of the models that the selected X-ray CT scanning instrument is sensitive to and the one or more effective material properties of the models that the selected EM tomography scanning instrument is sensitive to into the estimate of the value of the one or more material properties.

In the present invention, the term "sensitive" is used it the context of the sensitivity of the X-ray CT scanning instrument and the EM Tomography scanning instrument. In particular, a scanning modality, such as an X-ray CT (or, MECT) scanning instrument and an EM Tomography scanning instrument, is "sensitive to" a material property if this property can be accurately computed (or, reconstructed) from scan data provided by the specific scanning modality (i.e., with single modality imaging, without augmenting it by another modality), under normal scanning conditions, regardless of resolution. For example, X-ray CT scanning is sensitive to electron density and effective atomic number, and EM Tomography scanning is sensitive to electrical conductivity. In the alternative, X-ray CT scanning and EM Tomography scanning modalities are not "sensitive to" certain other material properties. In particular, X-ray CT scanning and EM Tomography scanning modalities (in a single modality imaging mode each) are not sensitive to the amount of hydrocarbon deposits in a given region of the object of interest. In the present invention, MECT is regarded as a single modality. Thus, the goal is to reconstruct a property of the object that each of the two modalities, when applied separately, are not sensitive to but become sensitive to when combined appropriately.

With reference to FIG. 2, in an additional embodiment, the training stage of the present invention may be further improved by including accuracy testing and optimization.

The flow diagram 200 of FIG. 2 includes additional method steps for improving the training stage. At operation 205, the method begins by providing a second plurality of models of the object of interest. The method continues at operation 210 by repeating computing the X-ray CT reconstruction for each of the second plurality of models of the object of interest and repeating computing the EM reconstruction for each of the second plurality of models of the object of interest to test an accuracy of the machine learning prediction model by comparing the estimated values of the one or more material properties with the one or more material properties computed from the plurality of models. The method also provides at operation 215 for modifying the 3D grid step size corresponding to the selected X-ray CT instrument resolution, the 3D grid step size corresponding to a selected electromagnetic (EM) tomography scanning instrument resolution and the desired 3D grid step size to optimize the machine learning prediction model. This optimization can be with respect to the model prediction accuracy, noise stability, range of applicability, and other criteria.

Accordingly, the present invention does not require implementing X-ray CT and EM Tomography inversion-based imaging during the initial training stage, which speeds up testing of various parameter settings. By testing these parameters, the goal is to get as close to practically realistic CT/EM Tomography specifications as possible.

FIG. 3 illustrates the operational stage of the present invention for the practical implementation of the system using the prediction model obtained during the training stage illustrated in FIG. 1 and FIG. 2.

The flow diagram 300 illustrating the operational stage shown in FIG. 3 begins at operation 305 by performing an X-ray CT scan of the object of interest to generate X-ray CT scan data of one or more objects of interest.

At operation 310, the method continues by performing an EM Tomography scan of the object of interest to generate EM Tomography scan data of the one or more objects of interest.

The method continues at operation 315 by reconstructing the one or more effective material properties of the models that the selected X-ray CT scanning instrument is sensitive to for the one or more objects of interest by inverting the X-ray scan data on the 3D grid having the 3D grid step size corresponding to the selected X-ray CT instrument resolution and at operation 320 by reconstructing the one or more effective material property of the models that the selected EM Tomography scanning is sensitive to for the one or more objects of interest by inverting the EM Tomography scan data on the 3D grid having the 3D grid step size corresponding to the selected EM Tomography scanning instrument resolution.

The method concludes at operation 325 by using the machine learning prediction model to estimate the value of the one or more material properties for the one or more objects of interest on the 3D grid having the desired 3D grid step size.

The following description is specific to an exemplary embodiment of the inventive system and method for imaging rock cores at wellsite operations using a Multi-Energy Computed Tomography (MECT) and Electrical Impedance Tomography (EIT) dual-modality system. MECT provides high resolution and high contrast between the solid phase and the liquid phase, but poor contrast between oil and water. EIT has a lower resolution, but a high contrast between solid or oil (insulators) and salty water (conductor). However, applications of the combined multi-modality imaging system are not restricted to imaging of rock cores and related Digital Rock (DR) analysis tasks performed at a wellsite or in a permanent geoscience center lab. For example, the inventive system and method can also be used for medical imaging, pre-clinical imaging, dental imaging, luggage scanning, and various other Non-Destructive Testing (NDT) applications. Accordingly, modifications of the method of the present invention and the use of other physical tomographic imaging modalities as applied in different industries are within the scope of the present invention.

Figure 4A:
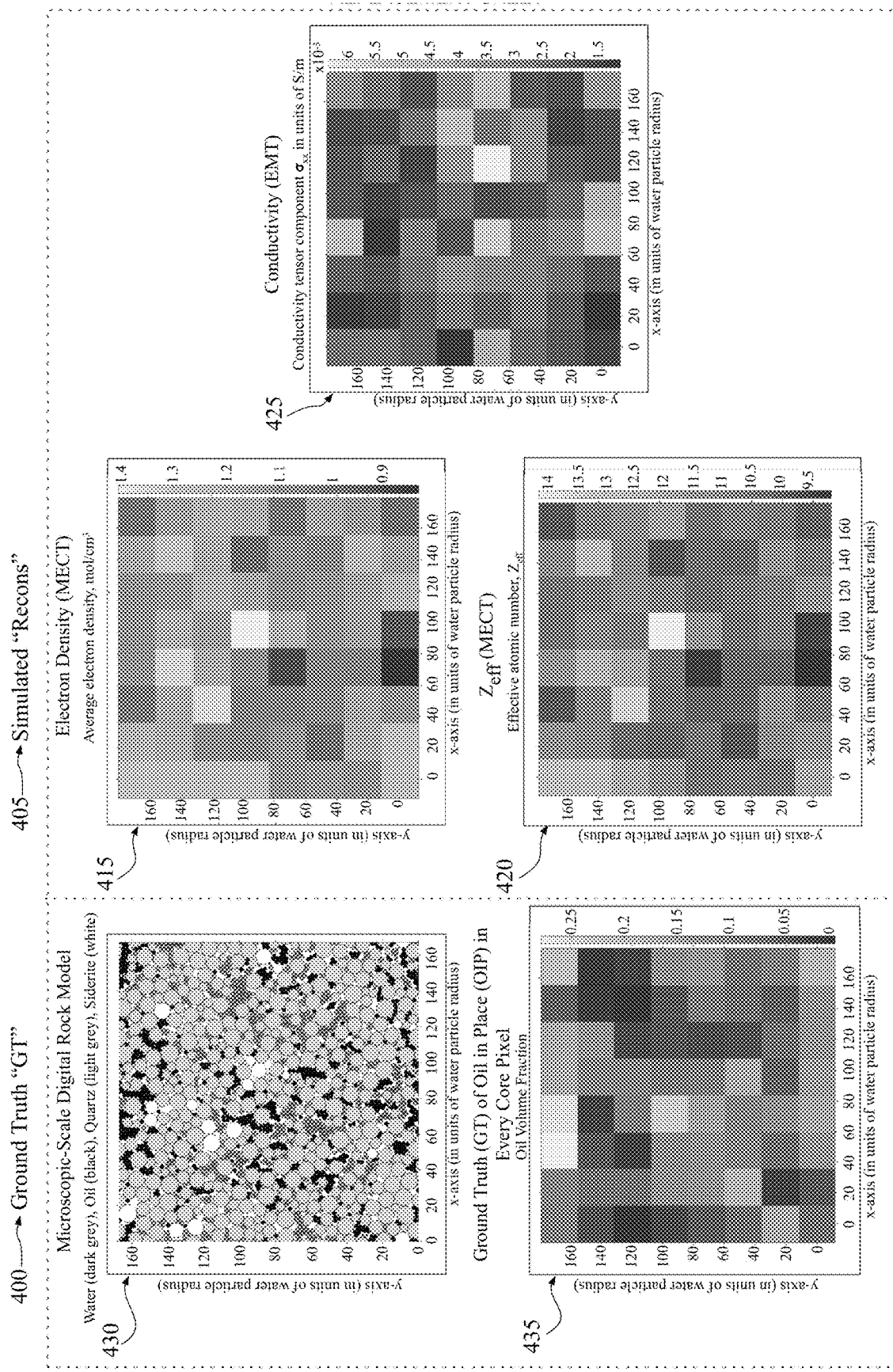
FIG. 4A is a diagram illustrating a first portion of an MECT-EMT workflow sample, from ground truth to oil in place (OIP) for a rock core, in accordance with an embodiment of the present invention.
Figure 4B:
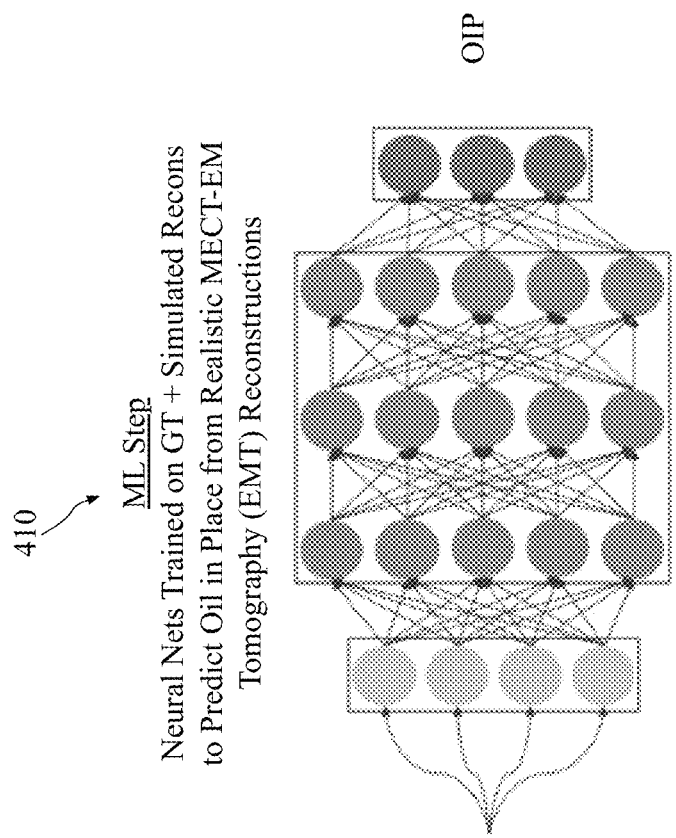
FIG. 4B is a diagram illustrating a second portion of an MECT-EMT workflow sample, from ground truth to oil in place (OIP) for a rock core, in accordance with an embodiment of the present invention.

With reference to FIG. 4A and FIG. 4B, in a particular embodiment, the one or more objects of interest may be a rock core and the estimate of the value of the one or more material properties may be a value of a hydrocarbon content of the rock core. The value of a hydrocarbon content of an object is the total amount of hydrocarbons (either of all types taken together, e.g., oil and natural gas, or taken separately) in a volume of predetermined size inside the object. These values can be computed in a volumetric fashion, i.e., for a multitude of small volumes arranged on a grid. As such, the novel core imaging workflow utilizing the described training steps in FIG. 1 and the operation steps in FIG. 3 may be applied in a specific application for determining the value of a hydrocarbon content of a rock core.

The method begins by providing a plurality of ground truth models of rock cores 400, wherein each of the plurality of the ground truth models of rock cores 400 comprising one or more predetermined material properties. FIG. 4A, illustrates the microscopic scale ground truth (GT) model of the rock cores 430 and the GT oil in place (OIP) in every pixel of the rock core 435. Accurate and high-resolution Digital Rock Simulation (DRS) may be implemented to provide the plurality of models. The realism of the simulation may be augmented by cross-checking its output with high quality measurements of real rock cores, using synchrotron nano-CT, Neutron Tomography (NT), Scanning Electron Microscope (SEM), and other high-resolution and/or high-contrast techniques. DRS allows simulating a variety of subsurface hydrocarbon-bearing formations and performing simulations for a specific formation, where the simulated digital rocks should be representative of the formation under evaluation.

The process continues at 405 by computing an X-ray computed tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray CT scanning instrument resolution. In the case of the rock core, the one or more effective material properties of the models that the selected X-ray CT scanning instrument is sensitive includes electron density ($\rho$) 415 and effective atomic number 420 ($Z_{eff}$). In a particular implementation, the volume-averaged X-ray CT attenuation is computed on a 3D grid at a chosen instrument resolution $L_{CT}$. If MECT modality is used, the attenuation is resolved as a function of X-ray energy, and may be converted to the effective atomic number ($Z_{eff}$) and average density ($\rho$), or another suitable basis.

Additionally, at 405 an electromagnetic (EM) reconstruction is computed for each of the plurality of models on a 3D grid by computing one or more effective material properties of the models that a selected EM Tomography scanning instrument is sensitive to for each of the plurality of models with a 3D grid step size corresponding to the selected EM tomography scanning instrument resolution. In the case of the rock core, the one or more effective material properties of the models that the selected EM Tomography scanning instrument is sensitive to is an effective tensor conductivity 425 ($\sigma$). At the operational stage of the invention, the values of $Z_{eff}$ and $\rho$ are reconstructed by inverting the MECT scan data and $\sigma$ is reconstructed by inverting EIT scan data on grids with step sizes $\sim L_{CT}$ and $\sim L_{EIT}$, respectively. At the training stage of the invention, these quantities can be computed directly from the ground truth models.

In a specific embodiment, the training workflow may include solving the inhomogeneous Laplace equation with suitably chosen boundary conditions, to simulate electric current within the DRS volume. The electrostatics may be simulated with a Finite-Element Method (FEM), Finite-Difference Method (FDM), Lattice Boltzmann Method (LBM), or any other suitable numerical method. The solution yields the electric field E and the current density governed by the Ohm's law J=$\sigma$E at a high resolution afforded by the DRS. The two vector fields are volume-averaged to a grid at a mesoscopic length scale $L_{EIT}$, which corresponds to the EIT instrument resolution. In general, the mesoscopic conductivity $\sigma = \langle J \rangle / \langle E \rangle$ will be a tensor, since the bulk-averaged vectors $\langle J \rangle$ and $\langle E \rangle$ are not necessarily co-linear. For most practical conditions, the mesoscopic conductivity can be accurately modelled with a tensor $\sigma$, which has 3×3=9 independent components, and thus requires 3 independent electrostatic simulations, realized with different boundary conditions. For reasonable rock cores, the tensor should be symmetric, with only 6 independent components.

The process steps at 400 and 405 are repeated for a number of randomly simulated rock cores with pre-determined properties, e.g., with a range of mineral compositions, bulk porosities, pore size distributions, tortuosity, wettability, etc. At step 405, for each of these cores, the method continues by computing the accurate value of HC content $S_{hc}$ on a grid of desired step size $L_S$. One can think of $S_{hc}$ as the total amount of HC in a cube with edge size $L_S$. Empirical functions are obtained that convert the triples of ($Z_{eff}$, $\rho$, $\sigma$) into $S_{hc}$. For improved robustness, a neural net can be trained that converts a patch of the maps of ($Z_{eff}$, $\rho$, $\sigma$) into the value $S_{hc}$ at the center of the patch.

At 410 of FIG. 4B, the method continues by training a machine learning prediction model to estimate a value of one or more of the material properties for each of the plurality of models on a 3D grid having a desired 3D grid step size, wherein the estimate of the value of the one or more material properties is determined based upon the computed X-ray CT reconstruction and computed EM reconstruction of each of the plurality of models. The machine learning prediction model comprises an empirical function to convert the one or more effective material properties of the one or more objects of interest that the selected X-ray CT scanning instrument is sensitive to and the one or more effective material properties of the one or more objects of interest that the selected EM tomography scanning instrument is sensitive to into the estimate of the value of the one or more material properties that both the selected X-ray CT scanning instrument and the selected EM tomography scanning instrument are not sensitive to. As shown in 410 of FIG. 4B, the neural net is trained on the GT 400 and simulated reconstructions 405 of FIG. 4A to predict hydrocarbon or oil in place (OIP) from realistic MECT-EMT reconstructions.

In operation, the empirical formulas (or the neural network), which are obtained during operation 410 of the training stage shown in FIG. 4B, to convert ($Z_{eff}$, $\rho$, $\sigma$) into subsurface hydrocarbon ($S_{hc}$). The formulas could be fairly simple (e.g., of a regression type) or more complicated (based on the application of a neural network). For improved accuracy of the conversion of ($Z_{eff}$, $\rho$, $\sigma$) into $S_{hc}$, the laboratory measurements of the relevant physical properties of core samples extracted from the formation may be incorporated at the training stage.

To test the system, the above operations are repeated for a number of new randomly simulated cores from the same general class of models representative of the given formation and the estimated $S_{hc}$ is compared with ground truth. Alternatively, the training stage method of the present invention can be tested on real tomographic core scan data.

In an exemplary embodiment for determining the required instrument resolutions $L_{CT}$ and $L_{EIT}$ in step 405 to achieve a desired accuracy (e.g., 10%) of $S_{hc}$ for a given rock formation, which will indicate the spatial resolution that each corresponding modality needs to achieve. The method additionally performs numerical experiments to assess how sensitive the computation of $S_{hc}$ is with respect to errors in $(Z_{eff}, \rho, \sigma)$. This will indicate the accuracy that each corresponding modality needs to achieve. In a different embodiment, the instrument resolutions $L_{CT}$ $^{and}$ $L_{EIT}$ are known and fixed, and the method determines the accuracy of estimating $S_{hc}$ for a given rock formation. In an additional embodiment, the resolutions $L_{CT}$ $^{and}$ $L_{EIT}$ are fixed, and the method determines the properties of the rock formation (range of mineral compositions, bulk porosity, pore size distribution, tortuosity, wettability, etc.), that could be imaged provided the desired accuracy of $S_{hc}$ is maintained.

Additional tests of the complete workflow may be performed using, as input, the values of $(Z_{eff}, \rho, \tau)$ expected from MECT and EIT reconstructions for randomly selected models or by using data obtained in experiments with cores representative of the formation being explored.

In the training stage of the invention, for improved robustness, the solution may be constrained by using low resolution values that are typically obtained from wireline or logging while drilling (LWD) measurements. This will also indicate which of the various wireline/LWD measurements are the most informative.

For improved robustness in the training stage, the class of simulated digital rocks in operation 400 can be constrained to reduce the amount of non-uniqueness, so that the conversion of $(Z_{eff}, \rho, \sigma)$ into $S_{hc}$ is as accurate as possible.

While the exemplary embodiment illustrated in the flow diagrams of FIG. 1-FIG. 4A and FIG. 4B utilizes a dual modality system comprising MECT and EIT, other embodiments are possible. Other embodiments may include combining complementary imaging modalities other than CT and EIT. For example, one modality of the dual modality system may have high spatial resolution, but low contrast resolution and the other, complementary, modality may have low spatial resolution, but high contrast resolution. The number of imaging modalities to be combined in the proposed system of the present invention may exceed two. For example, CT, EIT, and Magnetic Resonance Imaging (MRI/NMR) may be combined to perform multi-modality imaging. Various other combinations of imaging systems are within the scope of the invention.

In an exemplary embodiment, the present invention may be implemented at a wellsite to estimate hydrocarbon (HC) distribution throughout large rock cores (e.g., 3-4-inch diameter and 3-4-ft long) using imaging technologies having throughput, accuracy, and resolution that are practically acceptable for making wellsite operational decisions. In different embodiments, the present invention may be tailored to estimate other quantities of interest, for example, but not limited to, the water saturation, overall microporosity, etc.

Figure 5:
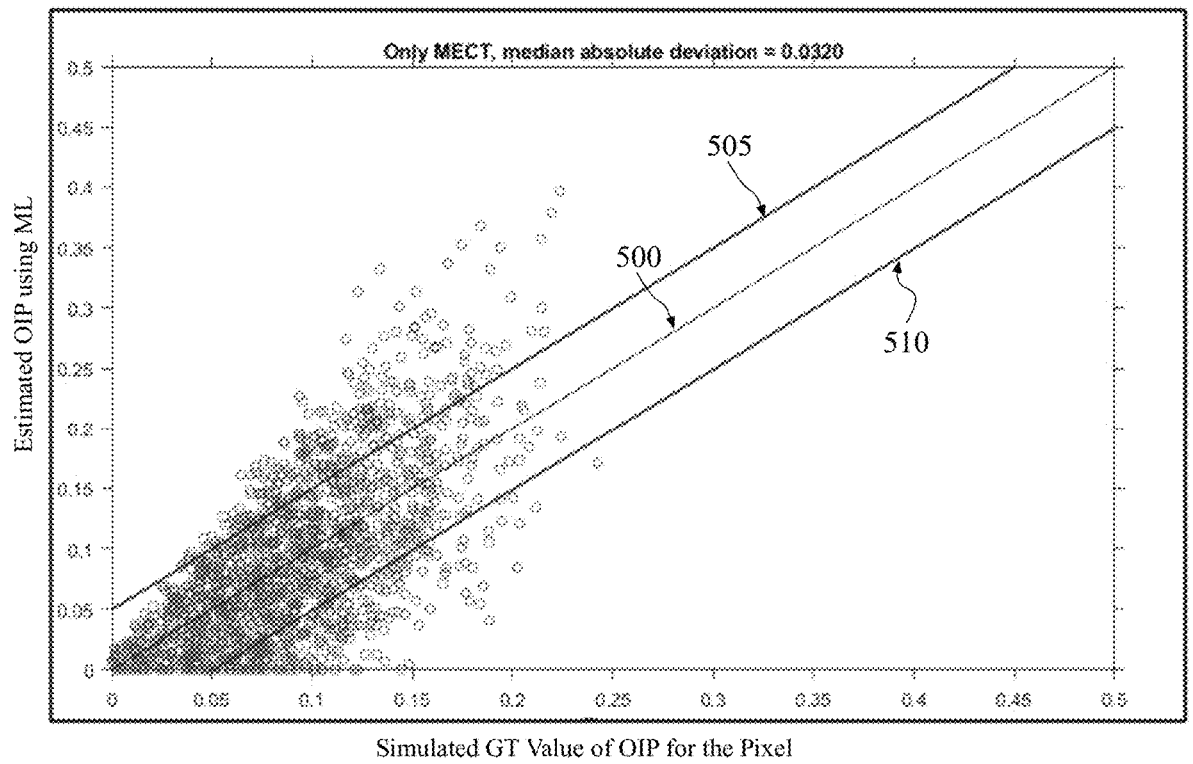
FIG. 5 is a graphical illustration of an oil in place (OIP) estimate for a rock core employing only an X-Ray CT scanning modality. The X- & Y-coordinates are the simulated ground truth values of OIP for the pixel, and the estimated OIP using machine learning, respectively.

FIG. 5 illustrates the results of an estimation of the OIP performed using only X-ray CT scanning with MECT. Following the ML training, a new set of ground truth (GT) rock core models and corresponding simulated reconstructions were generated. The circles on the graph in FIG. 5 represent mesoscopic pixels of the core. The X- & Y-coordinates are the simulated GT value of OIP for the pixel, and the estimated OIP using ML, respectively. If the formula using only the X-ray CT scanning training methodology were 100% accurate, all the circles would line up along the diagonal line x=y 500. The spread of the circles around the line x=y 500 illustrates the error of the estimation, wherein lines 505, 510 represent the 5% error boundaries.

Figure 6:
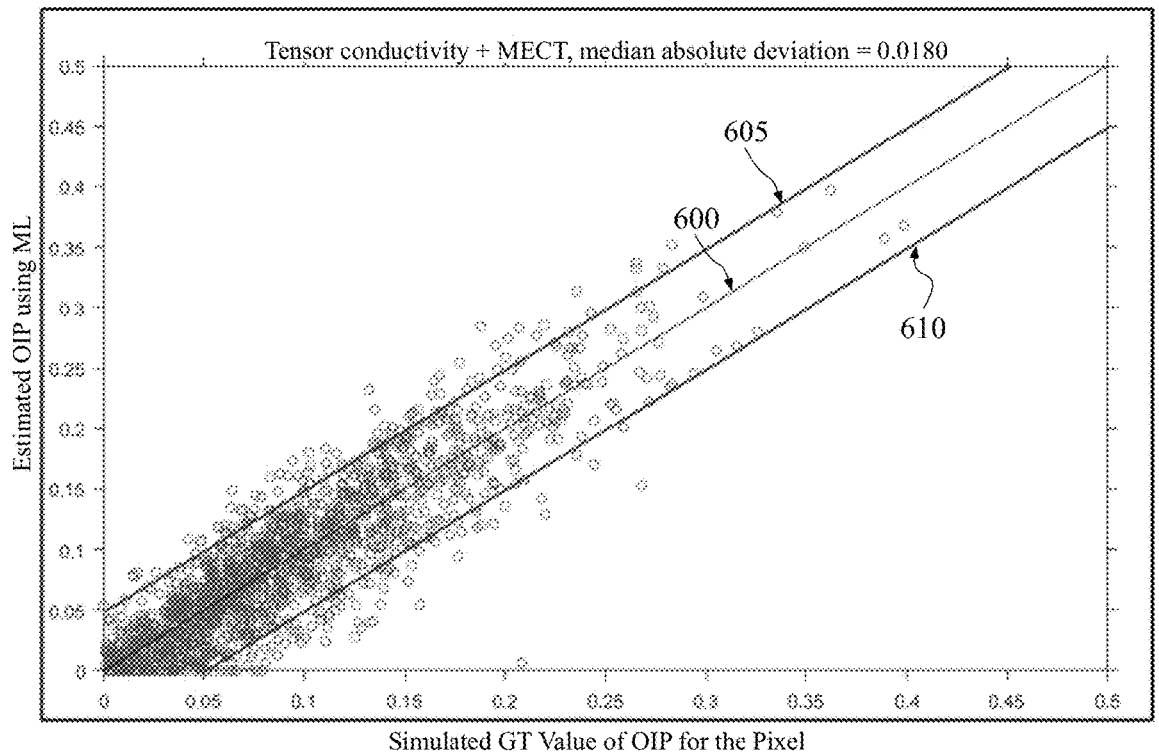
FIG. 6 is a graphical illustration of an oil in place (OIP) estimate for a rock core employing an X-Ray CT scanning modality and an EM Tomography dual-scanning modality, in accordance with an embodiment of the present invention. The X- & Y-coordinates are the simulated ground truth values of OIP for the pixel, and the estimated OIP using machine learning, respectively.

FIG. 6 illustrates the results of an estimation of the OIP performed using both the X-ray CT scanning with MECT and EM Tomography scanning with EMT, in accordance with the workflow example of the embodiment shown in FIG. 4. Following the ML training, a new set of ground truth (GT) rock core models and corresponding simulated reconstructions were generated. The circles on the graph in FIG. 6 represent mesoscopic pixels of the core. The X- & Y-coordinates are the simulated GT value of OIP for the pixel, and the estimated OIP using ML, respectively. If the formula using only the X-ray CT scanning and EM Tomography scanning training methodology were 100% accurate, all the circles would line up along the diagonal line x=y 600. The spread of the circles around the line x=y 600 illustrates the error of the estimation, wherein lines 605, 610 represent the 5% error boundaries.

A visual comparison of FIG. 5 and FIG. 6 clearly shows the advantage of adding EMT to MECT, wherein a greater percentage of the estimated OIL are within the 5% error boundaries.

The inventive method described with reference to FIG. 1-FIG. 6 on the whole provides a better HC estimate than what is possible to achieve with either of the scans (MECT or EIT) by itself. The approach can be used in a single imaging modality mode as well for estimating properties of cores to which this modality is sensitive. One example is to estimate rock core porosity with CT. For the vast majority of micro-CT scanners, a significant amount of porosity is below the scanner resolution limit. Using the described above training stage of FIG. 1, a neural network may be able to estimate the 3D distribution of the true effective core porosity without actually directly seeing all the pores. Additionally, this approach can be applied to accurately estimate the 3D distribution of other effective medium parameters (e.g., permeability) either in the single modality or multi-modality (two or higher) regimes.

The present invention may be embodied on various computing platforms that perform actions responsive to software-based instructions. The following provides an antecedent basis for the information technology that may be utilized to enable the invention.

The computer implemented method for performing multi-modality non-destructive tomographic imaging of one or more objects of interest in accordance with the present invention may be stored on a computer readable medium which may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like, scripting languages such as MATLAB, Python or the like, and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Further, for purposes of discussing and understanding the embodiments of the invention, it is to be understood that various terms are used by those knowledgeable in the art to describe techniques and approaches. Furthermore, in the description, for purposes of explanation, numerous specific details are set forth in order to provide a thorough understanding of the present invention. It will be evident, however, to one of ordinary skill in the art that the present invention may be practiced without these specific details. In some instances, well-known structures and devices are shown in block diagram form, rather than in detail, in order to avoid obscuring the present invention. These embodiments are described in sufficient detail to enable those of ordinary skill in the art to practice the invention, and it is to be understood that other embodiments may be utilized and that logical, mechanical, electrical, and other changes may be made without departing from the scope of the present invention.

What is claimed is:

1. A computer implemented method for training a machine learning prediction model for performing multi-modality non-destructive tomographic imaging of an object of interest, the method comprising:
    providing a plurality of models of an object of interest, each of the plurality of models comprising one or more predetermined material properties;
    computing an X-ray Computed Tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray CT scanning instrument resolution;
    computing an Electromagnetic (EM) reconstruction for each of the plurality of models on a 3D grid by computing one or more effective material properties of the models that a selected EM Tomography scanning instrument is sensitive to for each of the plurality of models with a 3D grid step size corresponding to the selected EM Tomography scanning instrument resolution; and
    training a machine learning prediction model to estimate a value of one or more of the material properties for each of the plurality of models on a 3D grid having a desired 3D grid step size, wherein the estimate of the value of the one or more material properties is determined based upon the computed X-ray CT reconstruction and computed EM reconstruction of each of the plurality of models.

2. The method of claim 1, wherein the machine learning prediction model comprises an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

3. The method of claim 2, further comprising:
    performing an X-ray CT scan of the object of interest to generate X-ray CT scan data of one or more objects of interest;

performing an EM Tomography scan of the object of interest to generate EM Tomography scan data of the one or more objects of interest;

reconstructing the one or more effective material properties of the models that the selected X-ray CT scanning instrument is sensitive to for the one or more objects of interest by inverting the X-ray scan data on the 3D grid having the 3D grid step size corresponding to the selected X-ray CT instrument resolution;

reconstructing the one or more effective material property of the models that the selected EM Tomography scanning is sensitive to for the one or more objects of interest by inverting the EM Tomography scan data on the 3D grid having the 3D grid step size corresponding to the selected EM Tomography scanning instrument resolution; and using the machine learning prediction model to estimate the value of the one or more material properties for the one or more objects of interest on the 3D grid having the desired 3D grid step size.

4. The method of claim 3, wherein the one or more objects of interest is a rock core.

5. The method of claim 4, wherein the estimate of the value of the one or more material properties is a value of a hydrocarbon (HC) content of the rock core.

6. The method of claim 5, wherein the estimate of the value of the one or more material properties is performed at a wellsite within a timeframe such that the rock core is in substantially the same condition as it was in the ground, wherein substantially the same condition means that the HC saturation inside the core has not changed.

7. The method of claim 1, wherein the plurality of models of the object of interest is a first plurality of models of the object of interest, the method further comprising:

providing a second plurality of models of the object of interest;

repeating computing the X-ray CT reconstruction for each of the second plurality of models of the object of interest and repeating computing the EM reconstruction for each of the second plurality of models of the object of interest to test an accuracy of the machine learning prediction model by comparing the estimated values of the one or more material properties with one or more material properties computed from the plurality of models.

8. The method of claim 1 further comprising modifying the 3D grid step size corresponding to the selected X-ray instrument resolution, the 3D grid step size corresponding to a selected Electromagnetic (EM) Tomography scanning instrument resolution and the desired 3D grid step size to optimize the machine learning prediction model.

9. The method of claim 1, wherein training the machine learning prediction model to determine the estimate of the value of the one or more material properties for each of the plurality of models on the 3D grid having a desired 3D grid step size further comprises, obtaining an empirical function to convert the one or more effective material properties of the models that the selected X-ray CT scanning instrument is sensitive to and the one or more effective material properties of the models that the selected EM Tomography scanning instrument is sensitive to into the estimate of the value of the one or more material properties.

10. The method of claim 1, wherein training the machine learning prediction model to determine the estimate of the value of the one or more material properties for each of the plurality of models on the 3D grid having a desired 3D grid step size further comprises, training a neural network to convert the one or more effective material properties of the models that the selected X-ray CT scanning instrument is sensitive to and the one or more effective material properties of the models that the selected EM Tomography scanning instrument is sensitive to into the estimate of the value of the one or more material properties.

11. The method of claim 1, wherein the one or more effective material properties of the models that the selected X-ray CT scanning instrument is sensitive to are selected from electron density and effective atomic number.

12. The method of claim 1, wherein the selected X-ray CT instrument is a multi-energy computed tomography (MECT) instrument.

13. The method of claim 1, wherein the selected EM Tomography scanning instrument is an Electrical Impedance Tomography (EIT) instrument.

14. The method of claim 1, wherein the one or more effective material properties of the models that the selected EM Tomography scanning instrument is sensitive to is selected from an effective scalar conductivity and an effective tensor conductivity.

15. A computer implemented method for performing multi-modality non-destructive tomographic imaging of one or more objects of interest, the method comprising:

performing an X-ray Computer Tomography (CT) scan of one or more objects of interest using a selected X-ray CT instrument to generate X-ray CT scan data of the one or more objects of interest;

performing an EM Tomography scan of the one or more objects of interest using a selected EM Tomography scanning instrument to generate EM Tomography scan data of the one or more objects of interest;

reconstructing one or more effective material properties of the one or more objects of interest that the selected X-ray CT scanning instrument is sensitive to by inverting the X-ray CT scan data on a 3D grid having a 3D grid step size corresponding to a resolution of the selected X-ray CT instrument;

reconstructing one or more effective material properties of the one or more objects of interest that the selected EM Tomography scanning instrument is sensitive to by inverting the EM Tomography scan data on a 3D grid having a 3D grid step size corresponding to a resolution of the selected EM Tomography scanning instrument resolution; and using a machine learning prediction model to estimate a value of one or more material properties for the one or more objects of interest on a 3D grid having a desired 3D grid step size, wherein the machine learning prediction model comprises an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

16. The method of claim 15, wherein the one or more objects of interest is a rock core.

17. The method of claim 16, wherein the estimate of the value of the one or more material properties is a value of a hydrocarbon (HC) saturation content of the rock core.

18. The method of claim 17, wherein the estimate of the value of the one or more material properties is performed at a wellsite within a timeframe such that the rock core is in substantially the same condition as it was in the ground, wherein substantially the same condition means that the HC saturation inside the core has not changed.

19. The method of claim 15, wherein the machine learning prediction model comprises a neural network to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties.

20. The method of claim 15, wherein the one or more effective material properties of the one or more objects that the selected X-ray CT scanning instrument is sensitive to are selected from an electron density and an effective atomic number.

21. The method of claim 15, wherein the selected X-ray CT scanning instrument is a multi-energy computed tomography (MECT) instrument.

22. The method of claim 15, wherein the selected EM Tomography scanning instrument is an Electrical Impedance Tomography (EIT) instrument.

23. The method of claim 15, wherein the one or more effective material properties of the one or more objects of interest that the selected EM Tomography scanning instrument is sensitive to is selected from an effective scalar conductivity and an effective tensor conductivity.

24. One or more non-transitory computer-readable media having computer-executable instructions for performing computer-executable instructions for performing a method of running a software program on a computing device for training a machine learning prediction model for providing a multi-modality non-destructive tomographic imaging method for one or more objects of interest, the method including issuing instructions from the software program comprising:
providing a plurality of models of an object of interest, each of the plurality of models comprising one or more predetermined material properties;
computing an X-ray Computed Tomography (CT) reconstruction for each of the plurality of models on a 3D grid by computing one or more effective material properties of the models that a selected X-ray CT scanning instrument is sensitive to for each of the plurality of models with a 3D grid step size corresponding to the selected X-ray CT instrument resolution;
computing an Electromagnetic (EM) reconstruction for each of the plurality of models on a 3D grid by computing one or more effective material properties of the models that a selected EM Tomography scanning instrument is sensitive to for each of the plurality of models with a 3D grid step size corresponding to the selected EM Tomography scanning instrument resolution; and training a machine learning prediction model to estimate a value of one or more of the material properties for each of the plurality of models on a 3D grid having a desired 3D grid step size, wherein the estimate of the value of the one or more material properties is determined based upon the computed X-ray CT reconstruction and computed EM reconstruction of each of the plurality of models.

25. The media of claim 24, wherein the machine learning prediction model comprises an empirical function to convert the one or more effective material properties of the one or more objects of interest that the selected X-ray CT scanning instrument is sensitive to and the one or more effective material properties of the one or more objects of interest that the selected EM Tomography scanning instrument is sensitive to into the estimate of the value of the one or more material properties that both the selected X-ray CT scanning instrument and the selected EM Tomography scanning instrument are not sensitive to.

26. The media of claim 25, further comprising issuing instructions from the software program comprising:
performing an X-ray CT scan of the object of interest to generate X-ray CT scan data of one or more objects of interest;
performing an EM Tomography scan of the object of interest to generate EM Tomography scan data of the one or more objects of interest;
reconstructing the one or more effective material properties of the models that the selected X-ray CT scanning instrument is sensitive to for the one or more objects of interest by inverting the X-ray scan data on the 3D grid having the 3D grid step size corresponding to the selected X-ray CT instrument resolution;
reconstructing the one or more effective material property of the models that the selected EM Tomography scanning is sensitive to for the one or more objects of interest by inverting the EM Tomography scan data on the 3D grid having the 3D grid step size corresponding to the selected EM Tomography scanning instrument resolution; and
using the machine learning prediction model to estimate the value of the one or more material properties for the one or more objects of interest on the 3D grid having the desired 3D grid step size.

27. The media of claim 26, wherein the one or more objects of interest is a rock core.

28. The media of claim 27, wherein the estimate of the value of the one or more material properties is a value of a hydrocarbon (HC) saturation content of the rock core.

29. The media of claim 28, wherein the estimate of the value of the one or more material properties is performed at a wellsite within a timeframe such that the rock core is in substantially the same condition as it was in the ground, wherein substantially the same condition means that the HC saturation inside the core has not changed.

* * * * *